(12) United States Patent
Toller et al.

(10) Patent No.: US 8,132,460 B1
(45) Date of Patent: Mar. 13, 2012

(54) LASER INDUCED BOND DELAMINATION (75) Inventors: Steven M. Toller, Dublin, OH (US); Jeff L. Dulaney, Dublin, OH (US)

(73) Assignee: LSP Technologies, Inc., Dublin, OH (US)

( * ) Notice: Subject to any disclaimer, the term of this patent is extended or adjusted under 35 U.S.C. 154(b) by 183 days.

(21) Appl. No.: 12/435,448

(22) Filed: May 5, 2009

Related U.S. Application Data (63) Continuation-in-part of application No. 10/950,865, filed on Sep. 27, 2004, now Pat. No. 7,770,454, and a continuation-in-part of application No. 11/227,745, filed on Sep. 15, 2005.

(51) Int. Cl.
*G01N 29/04* (2006.01)
(52) U.S. Cl. .................. 73/588; 73/801; 73/842
(58) Field of Classification Search ............ 219/121.62, 219/121.64; 381/196; 73/588, 587, 590, 73/801, 815, 827, 842, 844, 845, 778–788
See application file for complete search history.

(56) References Cited

U.S. PATENT DOCUMENTS

| | | | |
|---|---|---|---|
| 4,004,456 A | 1/1977 | Vahaviolos | |
| 4,100,808 A * | 7/1978 | Evans et al. .................... | 73/588 |
| 4,207,771 A | 6/1980 | Carlos et al. | |
| 4,401,477 A | 8/1983 | Clauer et al. | |
| 4,545,018 A | 10/1985 | Clements et al. | |
| 4,824,250 A | 4/1989 | Newman | |
| 4,838,085 A | 6/1989 | Pellerin et al. | |
| 4,901,357 A | 2/1990 | Albright | |
| 4,972,720 A * | 11/1990 | Wu .................................. | 73/801 |
| 5,127,019 A | 6/1992 | Epstein et al. | |
| 5,269,778 A | 12/1993 | Rink et al. | |
| 5,438,402 A * | 8/1995 | Gupta .......................... | 356/35.5 |
| 5,473,315 A | 12/1995 | Holroyd | |
| 5,572,016 A | 11/1996 | Wood et al. | |
| 5,729,012 A | 3/1998 | Wood et al. | |
| 5,803,965 A | 9/1998 | Yoon | |
| 5,959,735 A * | 9/1999 | Maris et al. ................... | 356/632 |
| 5,965,877 A | 10/1999 | Wood et al. | |
| 6,008,887 A | 12/1999 | Klein et al. | |
| 6,238,187 B1 | 5/2001 | Dulaney et al. | |
| 6,282,964 B1 | 9/2001 | Hancock et al. | |
| 6,288,358 B1 | 9/2001 | Dulaney et al. | |

(Continued)

FOREIGN PATENT DOCUMENTS

GB 2225427 A 5/1990

OTHER PUBLICATIONS

Toller, et al., "Tape Overlay for Laser Bond Inspection", U.S. Appl. No. 11/873,705, filed Oct. 17, 2007.

(Continued)

*Primary Examiner* — J M Saint Surin
(74) *Attorney, Agent, or Firm* — Benjamen E. Kern (57) ABSTRACT

Methods, systems, and apparatuses are provided for creating bond delaminations in a controlled fashion within adhesively bonded structures. In one embodiment, a system for inducing a defect in a bond of a bonded article includes a laser and a laser processor head. The laser processor head includes a housing, a lens disposed within the housing, at least one magnet disposed within the housing, and at least one sensor disposed within the housing. The system is capable of applying a laser pulse of sufficient energy fluence to cause localized weaknesses in the bond.

14 Claims, 9 Drawing Sheets

U.S. PATENT DOCUMENTS

| | | |
|---|---|---|
| 6,373,876 B1 | 4/2002 | Dulaney et al. |
| 6,479,790 B1 | 11/2002 | Graham et al. |
| 6,512,584 B1 | 1/2003 | O'Loughlin et al. |
| 6,554,921 B2 | 4/2003 | Sokol et al. |
| 6,657,160 B2 | 12/2003 | Hackel et al. |
| 6,759,626 B2 | 7/2004 | Clauer et al. |
| 6,795,198 B1 * | 9/2004 | Fuchs et al. .......... 356/521 |
| 6,848,321 B2 | 2/2005 | Bossi et al. |
| 6,945,114 B2 | 9/2005 | Kenderian et al. |
| 7,131,331 B2 | 11/2006 | Bates |
| 7,150,193 B2 | 12/2006 | Lorraine et al. |
| 7,154,067 B2 | 12/2006 | Yoshii |
| 7,253,908 B2 | 8/2007 | Vaccaro et al. |
| 7,270,004 B2 | 9/2007 | Dickinson et al. |
| 7,507,312 B2 * | 3/2009 | Bossi et al. .......... 156/344 |
| 7,509,876 B1 | 3/2009 | Sokol et al. |
| 7,765,861 B2 * | 8/2010 | Jacquemin .......... 73/150 A |
| 2005/0120803 A1 | 6/2005 | Sokol et al. |
| 2008/0257048 A1 | 10/2008 | Walters et al. |

OTHER PUBLICATIONS

Sokol, et al., "Lamb Waves for Laser Bond Inspection," U.S. Appl. No. 11/873,571, filed Oct. 17, 2007.

Sokol, et al., "Laser Bond Inspection Using Annular Laser Beam", U.S. Appl. No. 12/396,081, filed Mar. 2, 2009.

* cited by examiner

LASER INDUCED BOND DELAMINATION

CROSS-REFERENCE TO RELATED APPLICATIONS

This application is a continuation-in-part of U.S. patent application Ser. No. 10/950,865, filed on Sep. 27, 2004, which claims priority to U.S. Provisional Application No. 60/507,076, filed on Sep. 26, 2003. This application is also a continuation-in-part of U.S. patent application Ser. No. 11/227,745, filed on Sep. 15, 2005, which claims priority to U.S. Provisional Application No. 60/610,102, filed on Sep. 15, 2004. The above-referenced cases are incorporated herein by reference in their entireties.

BACKGROUND

Presently, delamination of an adhesively bonded structure may be performed by inserting a strip or piece of TEFLON (or like substance) into the bond in an area where the defect is desired, prior to the parts of the structure being adhered. Adhesive is then applied to the parts to be adhered and directly over the TEFLON strips, and the structure is assembled. The surface of the TEFLON is very slick and non-porous, thereby preventing the adhesive from adhering well to the TEFLON. When the adhesive is cured, the area defined by the TEFLON strips becomes a void in the adhesive layer. This void is treated as a defect.

Another method is to introduce contaminants (e.g., mold release agent, wax) into the bond in an area where the defect is desired prior to the parts of the structure being adhered. Upon curing the adhesive, the contaminated area becomes a locally weak, defective section in the bond (in comparison to the rest of the bond). Still another method is to construct the bonded structure, then mechanically drive a wedge into the bond line, forcibly separating the bonded parts.

After the adhesive is cured, the bonded structures are mechanically stressed, and the local defects are monitored for growth (by, e.g., ultrasonic techniques or X-rays).

SUMMARY

In one embodiment, a method is provided for inducing a defect in a bond of a bonded article, the method comprising: providing the bonded article, the bonded article comprising a first article bonded to a second article; applying a pulse of laser energy onto a front surface of the first article; inducing a stress wave in the first article at least a portion of which propagates through the first article, through the bond, and through the second article, and at least partially reflects off of a back surface of the second article; wherein at least a portion of the reflected stress wave propagates back through the second article to at least the bond and is of sufficient magnitude to induce the defect in the bond.

In another embodiment, a method for repairing a bonded article is provided, the method comprising: providing the bonded article, the bonded article comprising a first part and a second part and comprising a bond with at least one defect; applying a plurality of laser pulses to a surface of the first part in an area at least partially surrounding the defect, the laser pulses comprising sufficient energy fluence to generate localized disbonds in the bond in the area at least partially surrounding the defect; and separating the first part from the second part.

In another embodiment, a method for creating stress relief points in a bonded article is provided, the method comprising: providing the bonded article comprising a first part and a second part adhered together with a bond; exposing a surface of the first part with a plurality of laser pulses in a predetermined geometric arrangement, wherein the laser pulses comprise sufficient energy fluence to cause localized weaknesses in the bond.

In another embodiment, a system for inducing a defect in a bond of a bonded article is provided, the system comprising: a laser; and a laser processor head comprising: a housing; a lens disposed within the housing; at least one magnet disposed within the housing; and at least one sensor disposed within the housing; wherein the system is capable of applying a laser pulse of sufficient energy fluence to cause localized weaknesses in the bond.

BRIEF DESCRIPTION OF THE DRAWINGS

The accompanying figures, which are incorporated in and constitute a part of the specification, illustrate various example systems and methods and are used merely to illustrate various example embodiments. It should be noted that various components depicted in the figures may not be drawn to scale, and that the angles and interferences depicted in the figures are presented for purposes of illustration only, and should not be considered in any way as limiting.

DETAILED DESCRIPTION

The present embodiments disclose methods, systems, and apparatuses for creating bond delaminations in a controlled fashion between parts that have previously been adhesively bonded together.

In one embodiment, an adhesively bonded structure may be constructed for the purpose of being placed into service, and may be randomly removed from a manufacturing line and tested as part of a batch control inspection. In another embodiment, an adhesively bonded structure may have already been placed into service for a period of time, then removed from service, subjected to bond defect generation, and then mechanically tested. In another embodiment, the bond delamination may be created in an internal bond—that is, in a bond that is not on an external joint. Thus, in various embodiments, an adhesively bonded structure may have bond defects generated at any bond line in the adhesively bonded structure and at any time during the adhesively bonded structure's lifetime. The structure can be constructed to full strength specifications with no apparent flaws within any areas of the adhesive bonds. After construction of the structure is completed, the bonded areas can be exposed to laser energy to create failures of the adhesive bond in geometric patterns designed for engineering tests, e.g., the effects of bond defect growth during fatigue stress tests may be monitored. Structures that were bonded incorrectly (e.g., the structure parts were misaligned) could be disassembled (either totally or partially), and the surface re-prepared and re-bonded correctly. The present embodiments will find use in any field in which any form of bonding technology is used, including, but not limited to, the aerospace, automotive, and construction industries.

The term "adhesive" (or other forms of the term) is non-limiting and is meant to include any form of bonding in which materials are bonded together, with or without metal fasteners, and may include, without limitation, adhesive bonding, welding, including ultrasonic welding and friction welding, soldering, and the like.

Figure 1A:
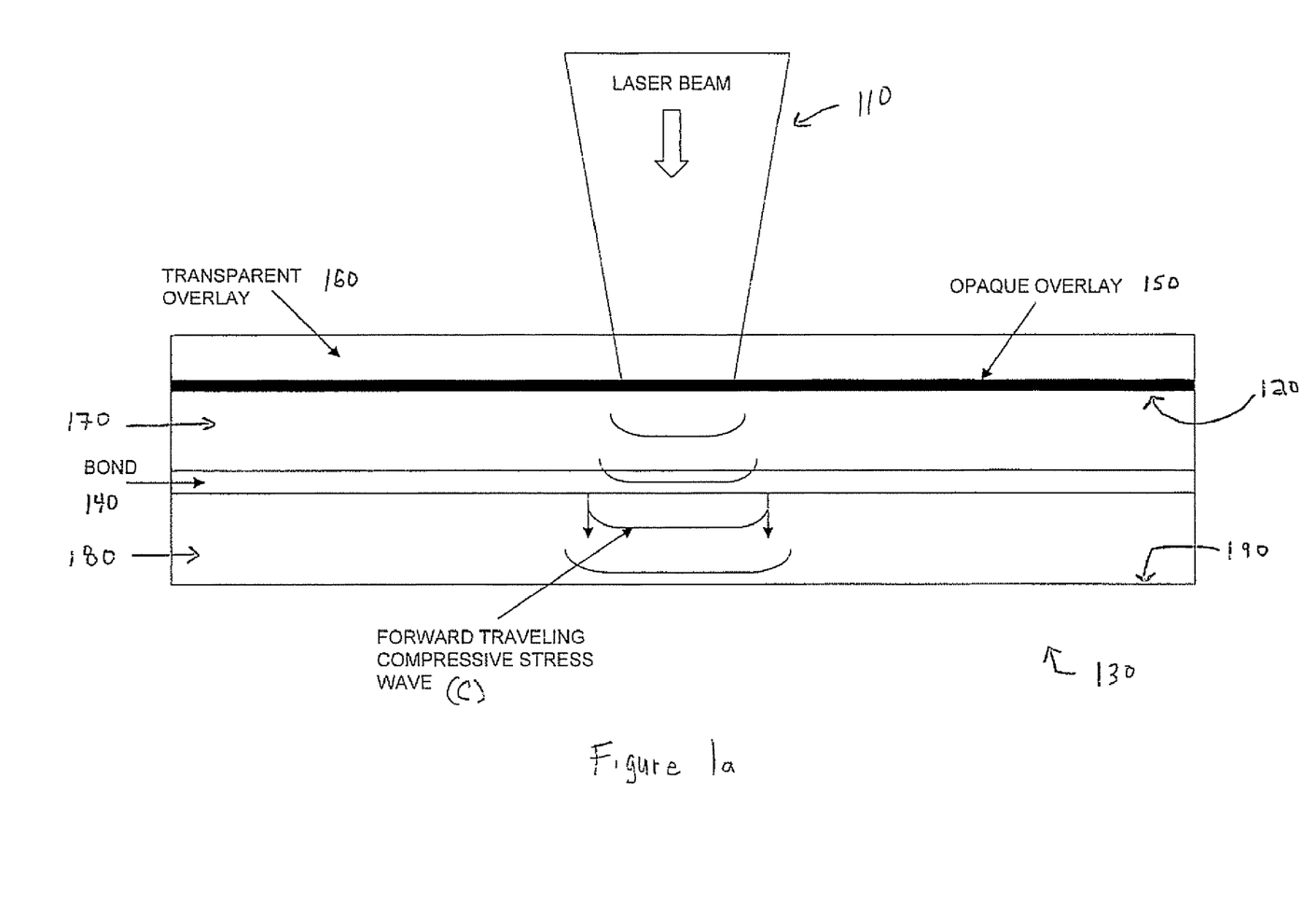
FIGS. 1a and 1b are schematic drawings that illustrate applications of a laser pulse to a bonded article.
Figure 1B:
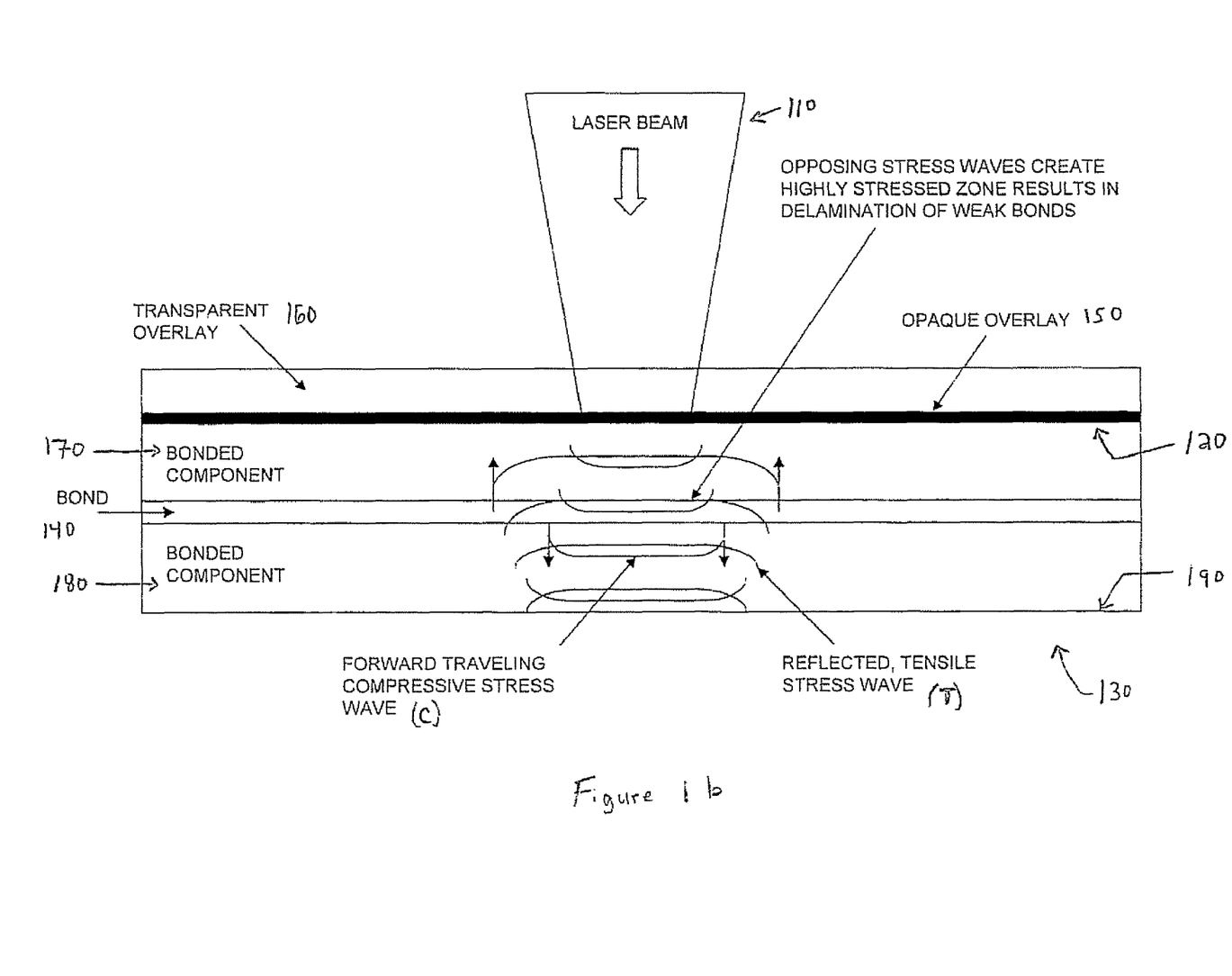

FIGS. 1a and 1b are schematic drawings that illustrate applications of a laser pulse to a bonded article, where the laser pulse comprises sufficient laser energy fluence to cause a localized defect in a bond of the bonded article. Referring to FIG. 1a, a pulse (or series of pulses) of laser energy 110 is applied to a surface 120 of a part 130 that has been adhesively bonded to one or more other parts. The application of pulse 110 may be directed directly above, or in close proximity to, an adhesive bond 140. Surface 120 of part 130 may first be covered with a protective, opaque overlay 150. The opaque overlay 150 may include, without limitation, tape, paint, or a liquid erosion-resistant coating as described in U.S. Pat. No. 7,268,317, which is incorporated herein by reference in its entirety. In the illustrated embodiment, the opaque overlay 150 is covered with a transparent overlay 160. In one embodiment, the transparent overlay is a layer of water. Other suitable transparent overlays include, but are not limited to, water-based solutions, other noncorrosive liquids, glass, quartz, sodium silicate, fused silica, potassium chloride, sodium chloride, polyethylene, fluoroplastics, nitrocellulose, and mixtures thereof. The transparent overlay may also be applied directly to the surface of the part. In other words, in one embodiment, no opaque overlay is applied.

In the illustrated embodiments, laser energy 110 is absorbed by opaque overlay 150, causing it to explosively vaporize. This rapid creation of a vapor cloud and plasma creates a high amplitude shock wave. The shock wave, being partially trapped by the transparent overlay 160, propagates as a compressive wave C through a first part 170 of adhesively bonded structure 130, through the bond 140, and through any subsequent parts (e.g., a second part 180) that are bonded to first part 170. When compressive wave C reaches the back surface 190 of the final part (e.g., second part 180), compressive wave C is reflected as a tensile wave T (see FIG. 1b). If the energy fluence of laser pulse 110 is sufficiently high, when tensile wave T reaches bond 140, bond 140 will at least partially fail. Laser energy fluence is defined as the laser energy per unit area on the work material. Stated another way:

$$\text{Fluence (Joules/cm}^2\text{)} = \frac{\text{laser pulse energy (J)}}{\text{focal spot area (cm}^2\text{)}}$$

Fluence can also be defined as the peak power per unit area:

$$\text{Fluence (Watts/cm}^2\text{)} = \frac{(\text{laser pulse energy (J)/laser pulse width (s)})}{\text{focal spot area (cm}^2\text{)}}$$

Figure 2:
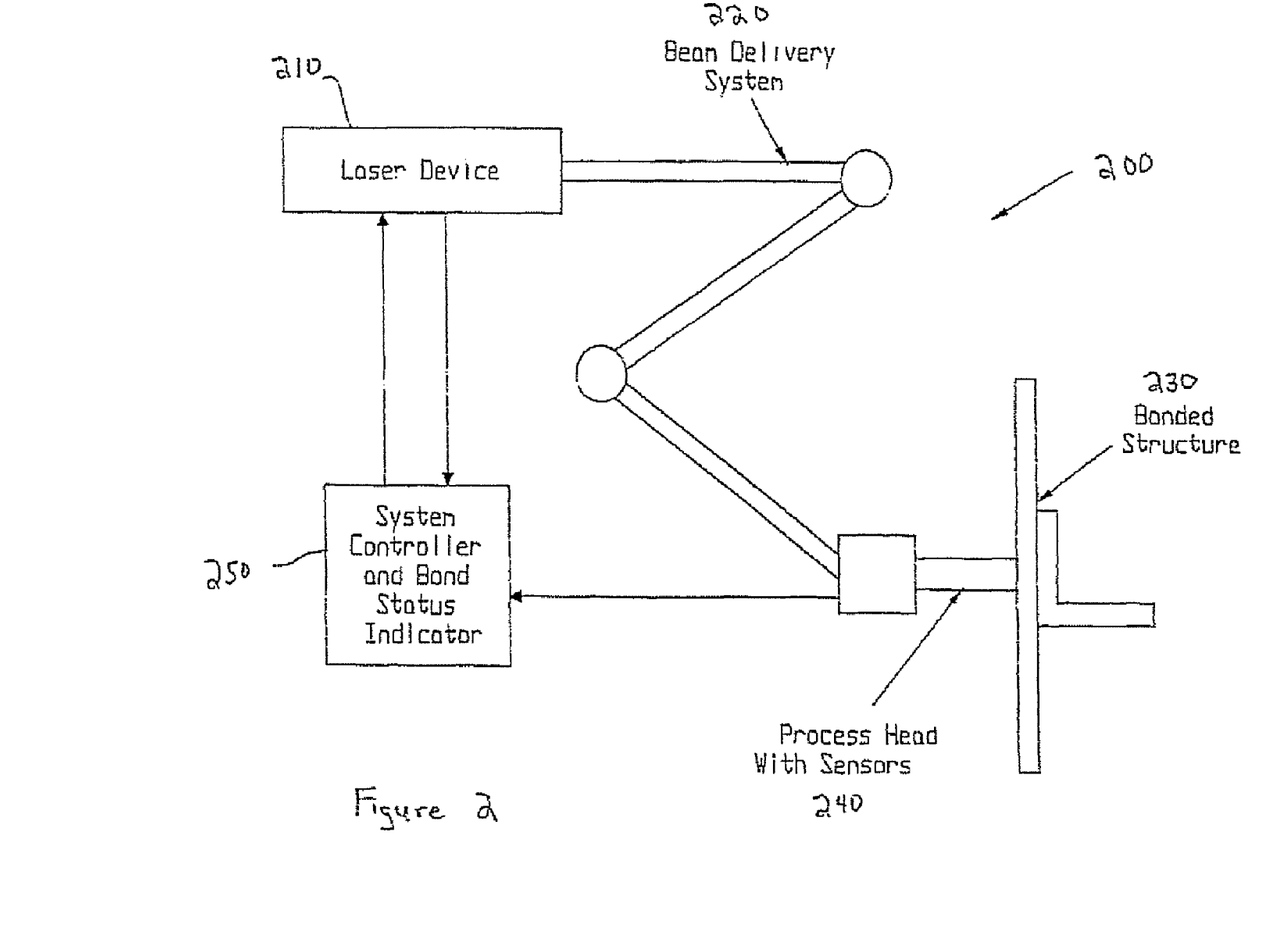
FIG. 2 illustrates an embodiment of a system 200 for creating a localized defect in a bond of a bonded article.

In one embodiment, the application of the laser pulse to the bonded article is performed in the context of system 200, an example of which is shown in FIG. 2. In the illustrated embodiment, system 200 includes a laser device 210 for generating the laser pulse or beam. System 200 also includes a beam delivery system 220 (generally depicted as an example form of an articulated arm assembly) for communicating the laser beam to the adhesively bonded structure 230. System 200 further includes a laser processing head 240 for providing an interface between the output of beam delivery system 220 and adhesively bonded structure 230, and further providing a sensor to collect measurement data from adhesively bonded structure 230. Alternatively, sensors external to the process head could also be used (e.g., VISAR, mechanical stress, or vibration sensors).

With continued reference to FIG. 2, system 200 further includes a system manager (e.g., a process controller 250), configured to provide various control functions and to process and evaluate the data (e.g., stress wave signature data) collected by the sensor of laser processing head 240.

In one embodiment, laser device 210 is capable of generating a laser beam having a pulsed emission. The laser energy may be delivered to the part in a short burst of light lasting 5000 ns or less. Generally speaking, the pulse width may have a width shorter than the width of the stress wave pulse desired for delamination of the bond of interest, in other words, the pulse width may be shorter than the transit time of a stress wave through the material at a given thickness. For example, the transit time in a 9 mm thick carbon-fiber reinforced epoxy composite might be 3 μs. Thus, in one embodiment, the stress wave (and, hence, the laser pulse) may be less than 3 μs (3000 ns).

The wavelength of the pulse may be any suitable wavelength that permits generation of a stress wave of sufficient magnitude to at least partially delaminate the bond in adhesively bonded structure 230. The pulse energy of the laser may be sufficient to provide a prescribed fluence over an area or areas with characteristic dimensions set in relation to the thickness and type of material being tested. In other words, the prescribed fluence may be of sufficient magnitude to produce a tensile stress wave capable of at least partially delaminating the bond of interest in adhesively bonded structure 230.

In one example, suitable laser parameters may include 1 to 100 J per pulse, 1 to 1000 ns pulse width, and 300 to 3000 nm wavelength. For example, an Nd:glass laser (1054 nm wavelength), a 20-300 as pulse width, and 3-50 J per pulse is suitable. In one embodiment, the beam has a flat-top spatial profile and a circular, rectangular, annular, or other geometrically shaped cross section. As a non-limiting example, suitable laser devices and configurations are provided in U.S. patent application Ser. Nos. 10/950,865 and 11/227,745. Other suitable laser devices and configurations are provided in U.S. Pat. Nos. 5,741,559, 5,911,891, 6,412,331, and 5,131,957, each of which is incorporated by reference herein in its entirety. In alternative embodiments, the laser's gain medium may be Nd:YAG, Nd:YLF, or any other solid state, liquid, or gaseous material suitable for generating a laser beam of sufficient fluence to cause bond delamination within a bonded structure.

In one embodiment, transportation of a laser beam may be accomplished via beam delivery system 220. Such transportation may be made in a precise, reliable, and reproducible manner. In FIG. 2, beam delivery system 220 is an articulated arm that has one end fixed relative to laser device 210. The fixed end of the arm receives the laser beam from laser device 210. Mirrors, such as custom mirrors with high damage threshold fluence, may be arranged inside of the atm at joints connecting each straight section of the arm. Each mirror typically turns the beam 90 degrees to a direction parallel with the axis of rotation of the joint. In one example arrangement, several such joints permit freedom of motion to locate the output end of the arm in any orientation to access an inspection point on a test article within reach of the arm. The arm also may serve as a safety enclosure for the laser beam.

One example of an articulated arm beam delivery system 220 is that manufactured by Laser Mechanisms, Inc. In one configuration, the arm receives a laser beam from laser device 210 and delivers it to laser processing head 240 coupled to the output end of the arm. The arm has several joints that allow an operator to move process head 240 over bonded structure 230 in a variety of operations.

It should be understood that any suitable mechanism may be used to facilitate transport of the laser beam to bonded structure 230. Additionally, any form of articulated arm assembly may be used. The delivery system may be flexible and selectively configurable to accommodate different access paths for guiding the laser beam to bonded structure 230, depending upon the inspection environment. The system may also include the ability to remotely generate and deliver the laser beam to bonded structure 230. Certain delamination environments may require serpentine-like propagation paths to access bonded structure 230. As such, beam delivery system 220 may be constructed so as to be capable of achieving the appropriate beam routing. Additionally, some applications will not accommodate a direct line-of-sight propagation path for the beam travel. Accordingly, beam delivery system 220 may effectuate direct and indirect beam communications between the laser and target.

In an alternative beam delivery setup, a fiber optic beam delivery system may be used. The fiber optic beam delivery system may be constructed such that the fiber system transmits the required energy without damage to the fiber. Either solid or hollow fibers may be used in this implementation. In one example, a fiber optic delivery system includes a single fiber or a multiplicity of fibers that could bend in a manner that would allow for delivery of the beam energy to a desired point on a complex structure.

Referring again to FIG. 2, laser processing head 240 may facilitate the interface between the output end of beam delivery system 220 and bonded structure 230 to be delaminated. In one embodiment, laser processing head 240 may be capable of concentrating the raw beam out of the articulated arm and delivering the concentrated beam to the work surface.

In one embodiment, system 200 (exclusive of the bonded structure 230) is fully mobile. In other words, in the example context of aircraft, system 200 may be readily moved from one location to another within the same airport, hanger, or carrier to process a given bonded structure 239 (e.g., part of an airplane); or system 200 may be moved from, e.g., hanger to hanger.

Figure 3:
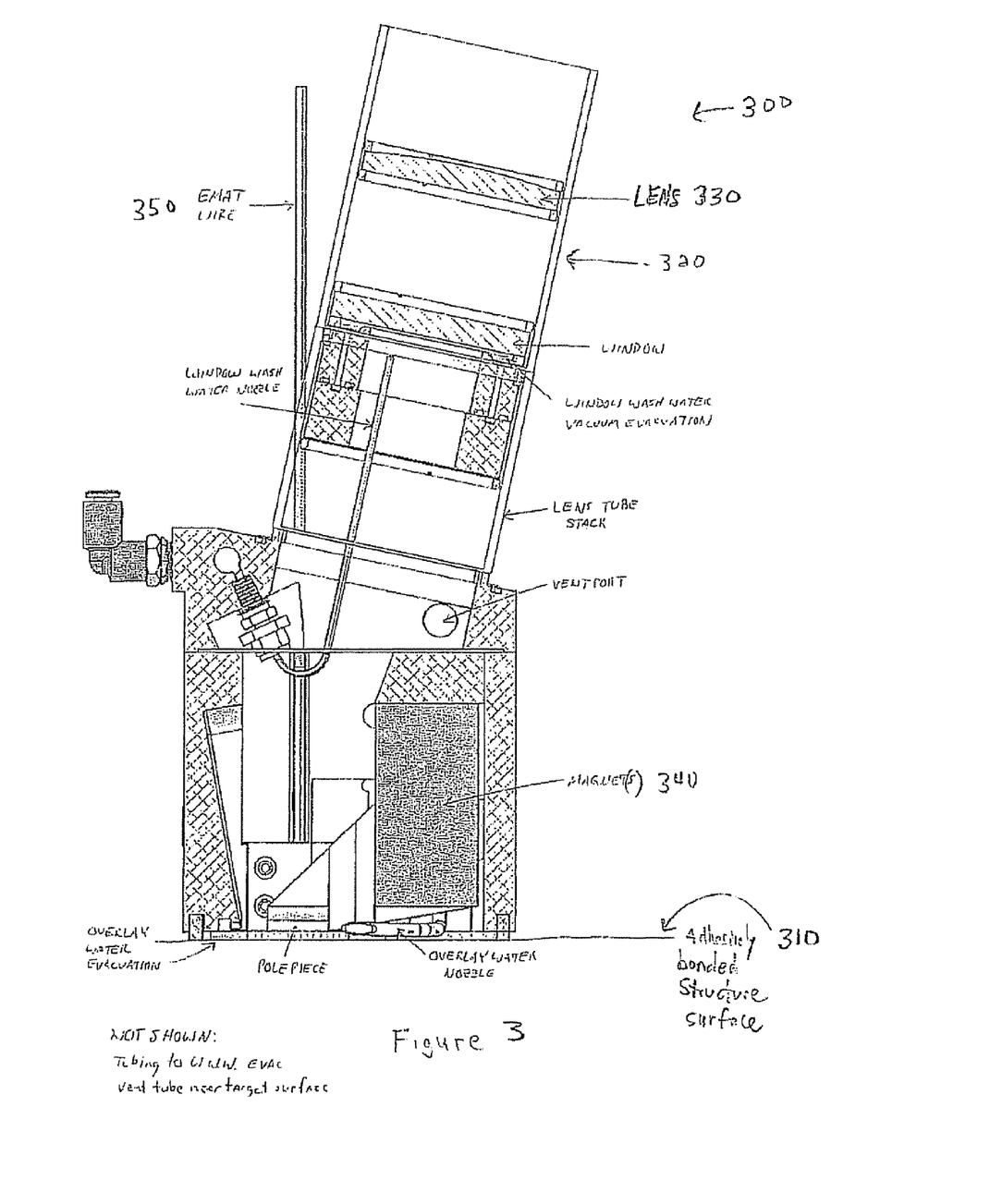
FIG. 3 illustrates an embodiment of a laser processing head.

FIG. 3 is a schematic diagrammatic view of one embodiment of a laser processing head 300 that facilitates delivery of a laser beam from an articulated arm to an adhesively bonded structure surface 310. The illustrated laser processing head 300 includes a housing 320. A lens 330 is disposed within housing 320. Further, at least one magnet 340 is disposed within housing 320, and at least one sensor 350 is at least partially disposed within housing 329.

Figure 4:
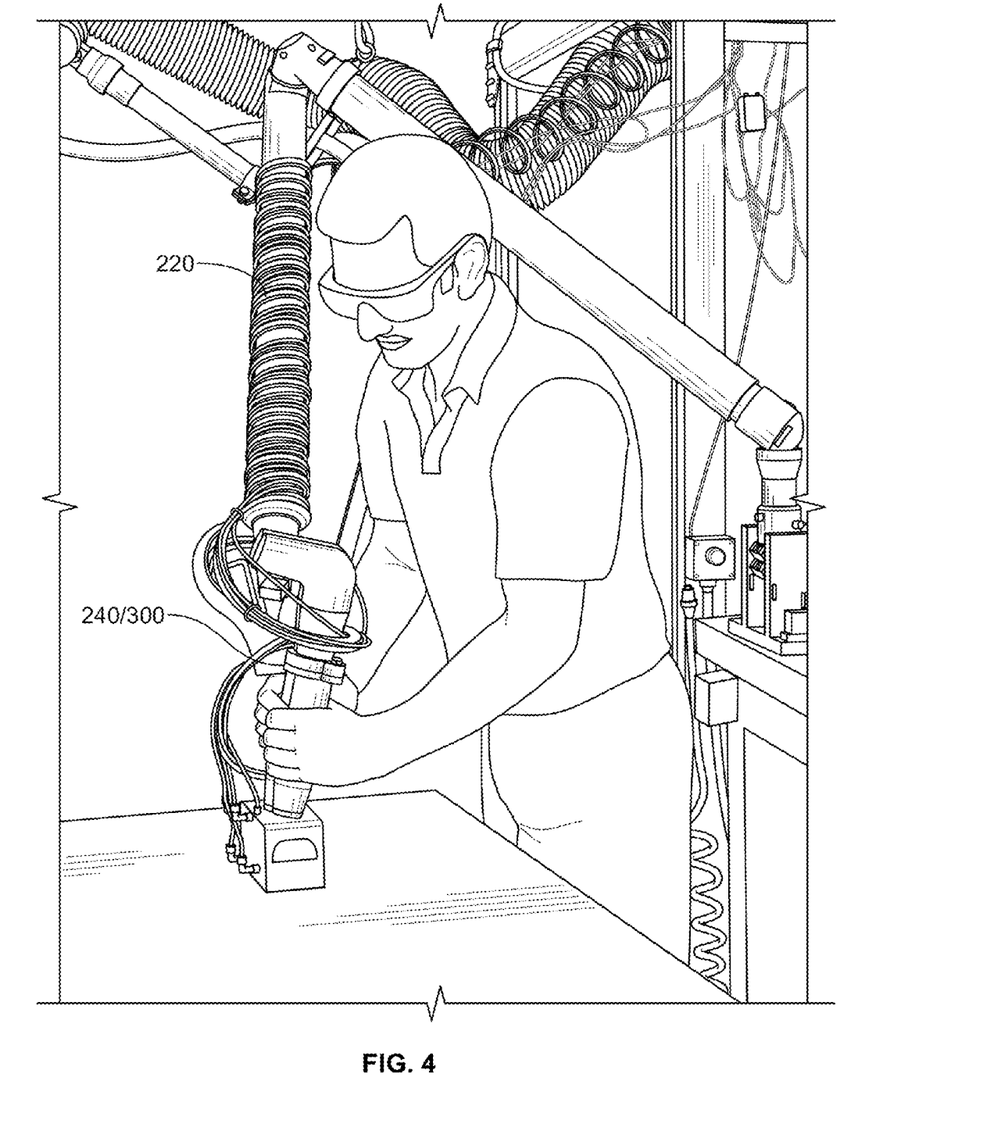
FIG. 4 illustrates an embodiment of a system 200 in an example operational environment.

FIG. 4 illustrates the example laser processing head 300 in an example operational environment. Other suitable systems are described in U.S. patent application Ser. Nos. 10/950,865 and 11/227,745.

Figure 5:
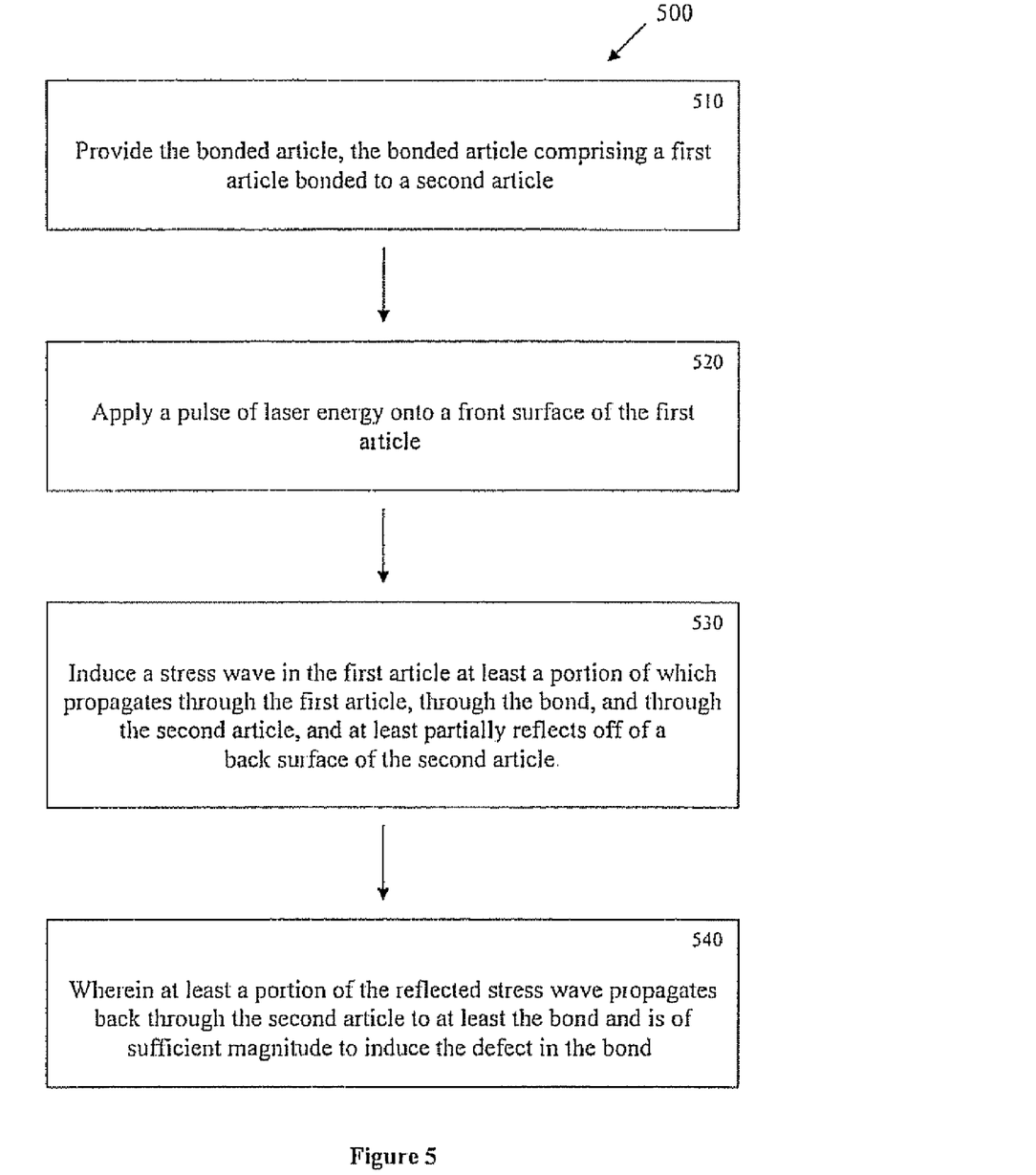
FIG. 5 illustrates a flow chart of one embodiment of a method for inducing a defect in a bond of a bonded article.

FIG. 5 illustrates a flow chart of an example method 590 for inducing a defect in a bond of a bonded article. The method comprises providing a bonded article, wherein the bonded article includes a first article bonded to a second article (510). The method further includes applying a pulse of laser energy onto a front surface of the first article (520). A stress wave is induced in the first article, such that at least a portion of the stress wave propagates through the first article, the bond, and the second article, and at least partially reflects off of a back surface of the second article (530). At least a portion of the reflected stress wave propagates back through the second article to at least the bond and is of sufficient magnitude to induce the defect in the bond (540).

Figure 6:
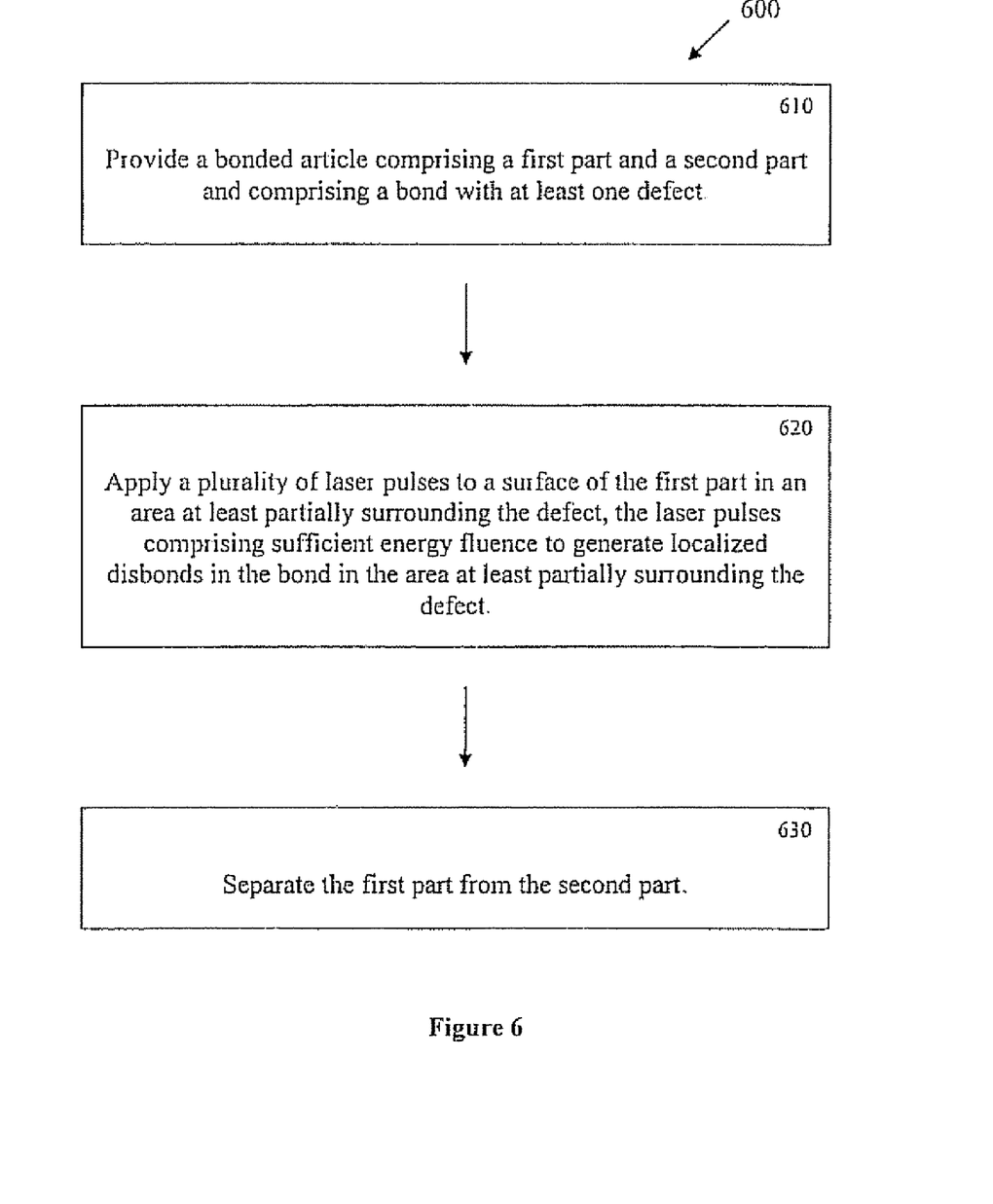
FIG. 6 illustrates a flow chart of one embodiment of a method for repairing a bonded article.

FIG. 6 illustrates a flow chart of an example method 600 for repairing a bonded article. The method comprises providing a bonded article including a first part, a second part, and a bond with at least one defect (610). A plurality of laser pulses is applied to a surface of the first part in an area at least partially surrounding the defect, wherein the laser pulses have sufficient energy fluence to generate localized disbonds in the bond in the area at least partially surrounding the defect (620). The method further includes separating the first part from the second part (630).

Figure 7:
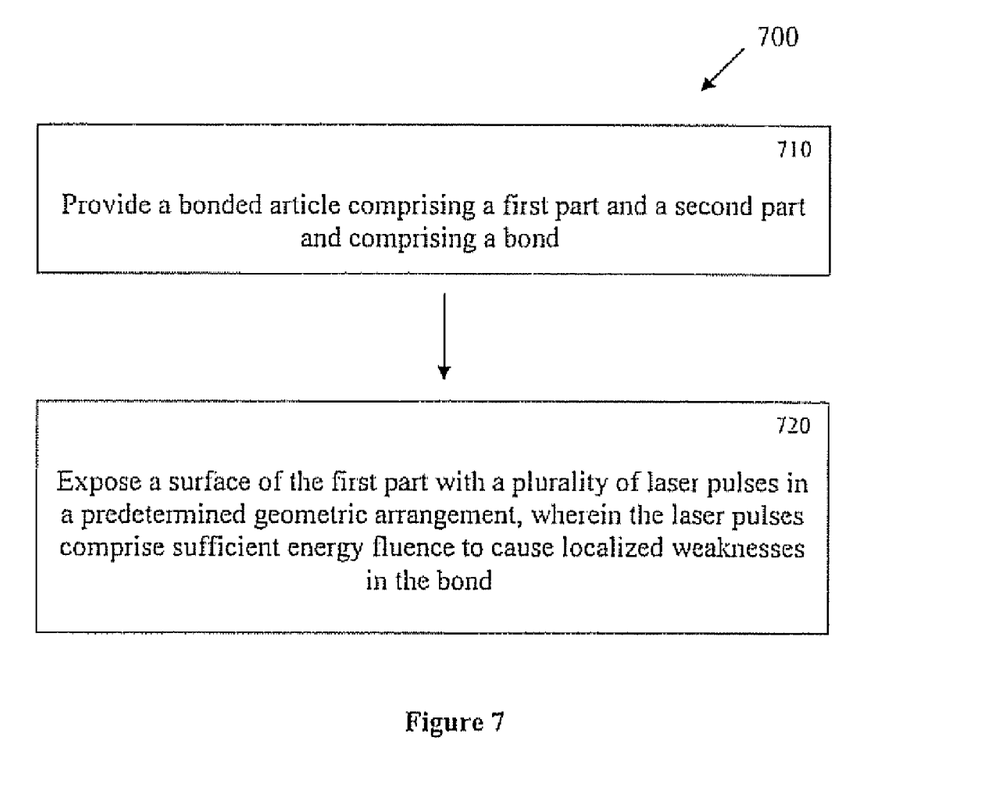
FIG. 7 illustrates a flow chart of one embodiment of a method for creating stress relief points in a bonded article.

FIG. 7 illustrates a flow chart of an example method 700 for creating stress relief points in a bonded structure. The method comprises providing a bonded article having a first part, a second part, and a bond (710). The method further includes exposing a surface of the first part with a plurality of laser pulses in a predetermined geometric arrangement, wherein the laser pulses comprise sufficient energy fluence to cause localized weaknesses in the bond (720).

With respect to any of the systems, methods, and apparatuses herein described, it is contemplated that the bonds may be inspected at any point before, intermittently, or after applying the laser pulse(s). Suitable laser bond inspection techniques are described in U.S. patent application Ser. Nos. 10/950,865, 11/227,745, 11/873,677, 11/873,705, and 11/873,571, all of which are incorporated herein by reference in their entireties.

EXAMPLES

A system as described and shown with respect to FIGS. 2, 3, and 4 was used to create disbonded patches at selected locations on the top and bottom skin surfaces of a 1.5×3×16 foot (approximately 45×90×490 cm) airplane wing. The wing was primarily fabricated through the use of adhesive bonding of laminated carbon fiber composite components with a heavy paste adhesive. The skin thickness of the wing varied from about 0.25 inches to about 0.75 inches (approximately 0.6 cm to approximately 1.9 cm). The skin was in the form of large sheets, including curved and flat sheets, bonded to an internal support frame structure. The support structure internal to the wing was also made from laminated carbon fiber composite. Most of the internal structure was about 0.2 inches to about 0.5 inches thick (approximately 0.5 cm to approximately 1.3 cm). Most of the internal structure components were in the form of I-beams or shapes that may be used where high strength and light weight are critical to a structure. The individual components were adhesively bonded together using a thick, paste style adhesive. The adhesive layer thickness typical varied from about 0.005 inches to 0.25 inches (approximately 0.01 cm to approximately 0.6 cm).

The exact locations, sizes, and geometries of the delamination defects were specified. An ultrasonic inspection probe was used to inspect the entire wing structure prior to laser exposure. The probe used ultrasonic sound waves to "look into" the structure and determine the thickness of the component with which the probe was in contact. The ultrasonic waves penetrated the wing skin and mapped out the locations of the internal support structure where the thickness was effectively increased. However, if the bond between the skin and the internal components was not adequately filled with adhesive (that is, a defect existed), the ultrasonic waves were not coupled into the internal components and the probe only recorded the thickness of the skin. The entire structure was ultrasonically mapped.

Figure 8:
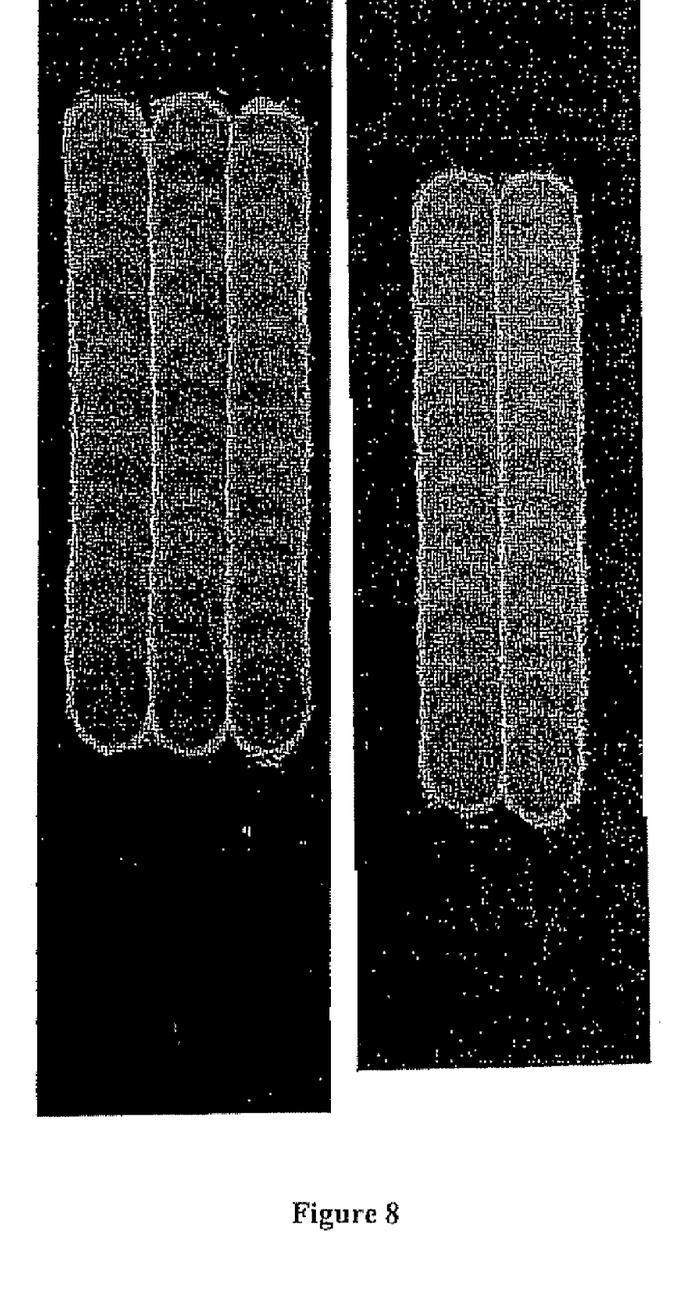
FIG. 8 illustrates an example shot configuration.

The nominal energy was set at approximately 22 J/cm² at a 100 ns pulse width. Spot size was 10 mm in diameter as determined by an approximately 5 J burn onto 3M® 471 black tape. Laser shots were taken with 50% overlap of both the rows and the columns. FIG. 8 illustrates an example shot configuration as shown on a piece of black tape.

Process patches were outlined directly on the wing with a grease pencil. The placement of laser processing head 300 was guided by following a grid template temporarily taped to the wing. Bond failures of 0.5×3 inches (approximately 1.3 cm×7.6 cm) up to 6×3 inches (approximately 15.2×7.6 cm) were created. The delaminations were of several different geometries, including rectangular, square, and semi-circular, although any other geometric shape is equally contemplated.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

Furthermore, while the systems, methods, and so on have been illustrated by describing examples, and while the examples have been described in considerable detail, it is not the intention of the applicant to restrict, or in any way, limit the scope of the appended claims to such detail. It is, of course, not possible to describe every conceivable combination of components or methodologies for purposes of describing the systems, methods, and so on provided herein. Additional advantages and modifications will readily appear to those skilled in the art. Therefore, the invention, in its broader aspects, is not limited to the specific details and illustrative examples shown and described. Accordingly, departures may be made from such details without departing from the spirit or scope of the applicant's general inventive concept. Thus, this application is intended to embrace alterations, modifications, and variations that fall within the scope of the appended claims. The preceding description is not meant to limit the scope of the invention. Rather, the scope of the invention is to be determined by the appended claims and their equivalents.

Finally, to the extent that the term "includes" or "including" or "having" is employed in the detailed description or the claims, it is intended to be inclusive in a manner similar to the term "comprising," as that term is interpreted when employed as a transitional word in a claim. Furthermore, to the extent that the term "or" is employed in the claims (e.g., A or B) it is intended to mean "A or B or both." When the applicants intend to indicate "only A or B, but not both," then the term "only A or B but not both" will be employed. Similarly, when the applicants intend to indicate "one and only one" of A, B, or C, the applicants will employ the phrase "one and only one." Thus, use of the term "or" herein is the inclusive, and not the exclusive use See Bryan A. Garner, A Dictionary of Modern Legal Usage 624 (2d. Ed. 1995).

What is claimed is:

1. A method for inducing a defect in a bond of a bonded article, the method comprising:
    providing a bonded article having at least two articles, including a first article bonded to a second article,
        wherein the bond between the first article and the second article has a strength which is substantially in accordance with a full strength specification;
    applying a pulse of laser energy to a front surface of the first article;
    inducing a stress wave in the first article such that at least a portion of the stress wave propagates through the first article, the bond, and the second article, and the stress wave at least partially reflects off a back surface of the second article, wherein at least a portion of the reflected stress wave propagates back through the second article to at least the bond and is of sufficient magnitude to induce a defect in the bond; and
    detecting the defect, wherein the detecting comprises electromagnetically detecting a stress wave signature.

2. The method of claim 1, further comprising inspecting the bond prior to applying the laser pulse.

3. The method of claim 1, further comprising inspecting the bond subsequent to applying the laser pulse.

4. The method of claim 1, further comprising monitoring bond defect growth by fatigue stress tests.

5. The method of claim 1, further comprising inspecting the bond by non-destructive means.

6. A method for repairing a bonded article, comprising:
    providing a bonded article having at least two parts, including a first part and a second part, the bonded article further including a bond with at least one defect,
        wherein the first part and the second part are bonded in substantial accordance with a full strength specification;
    applying a plurality of laser pulses to a surface of the first part in an area at least partially surrounding the defect, the laser pulses comprising sufficient energy fluence to generate localized disbonds in the bond in the area at least partially surrounding the defect;
    separating the first part from the second part; and
    inspecting the bond using laser bond inspection.

7. The method of claim 6, further comprising detecting the defect in the bond.

8. A method for creating stress relief points in a bonded article, comprising:
    providing a bonded article including at least two parts, including a first part and a second part adhered together with a bond,
        wherein the first part and the second part are bonded in substantial accordance with a full strength specification; and
    exposing a surface of the first part with a plurality of laser pulses in a predetermined geometric arrangement, wherein the laser pulses comprise sufficient energy fluence to cause localized weaknesses in the bond.

9. The method of claim 8, wherein the bond comprises at least one defect prior to exposing.

10. The method of claim 8, further comprising inspecting the bond using laser bond inspection.

11. The method of claim 8, further comprising detecting the localized weaknesses in the bond subsequent to the exposing.

12. A system for inducing a defect in a bond of a bonded article, comprising:
    a laser; and
    a laser processor head comprising a housing, a lens disposed within the housing, at least one magnet disposed within the housing, and at least one sensor disposed within the housing, wherein the system is capable of applying a laser pulse of sufficient energy fluence to cause localized weaknesses in the bond,
        wherein the bond has a strength which is substantially in accordance with a full strength specification prior to applying the laser pulse.

13. The system of claim 12, further comprising an articulated arm capable of delivering a laser beam from the laser to the laser processor head.

14. The system of claim 12, further comprising a controller.

* * * * *